US012702783B2

(12) United States Patent
Hansmann et al.

(10) Patent No.: US 12,702,783 B2
(45) Date of Patent: Aug. 11, 2026

(54) SUPPLY DEVICE AND PROCESS FOR SUPPLYING A PATIENT-SIDE COUPLING UNIT WITH A GAS MIXTURE

(71) Applicant: Drägerwerk AG & Co. KGaA, Lübeck (DE)

(72) Inventors: Hans-Ullrich Hansmann, Lübeck (DE); Oliver Garbrecht, Lübeck (DE); Hendrik Fischer, Lübeck (DE)

(73) Assignee: Drägerwerk AG & Co. KGaA, Lübeck (DE)

( * ) Notice: Subject to any disclaimer, the term of this patent is extended or adjusted under 35 U.S.C. 154(b) by 915 days.

(21) Appl. No.: 18/063,734

(22) Filed: Dec. 9, 2022

(65) Prior Publication Data

US 2023/0181863 A1 Jun. 15, 2023

(30) Foreign Application Priority Data

Dec. 14, 2021 (DE) ..................... 10 2021 132 927.2

(51) Int. Cl.
*A61M 16/20* (2006.01)
*A61M 16/12* (2006.01)
*A61M 16/00* (2006.01)

(52) U.S. Cl.
CPC ............ *A61M 16/12* (2013.01); *A61M 16/20* (2013.01); *A61M 2016/0027* (2013.01)

(58) Field of Classification Search
CPC .............. A61M 16/201; A61M 16/202; A61M 16/024; A61M 16/0891; A61M 16/107; A61M 16/18; A61M 16/204; A61M 16/208; A61M 16/125
See application file for complete search history.

(56) References Cited

U.S. PATENT DOCUMENTS

| | | | |
|---|---|---|---|
| 3,664,361 | A | 5/1972 | Bartels |
| 3,762,427 | A | 10/1973 | Mollering |
| 4,549,563 | A | 10/1985 | Monnier |
| 8,356,596 | B2 | 1/2013 | Brandt et al. |
| 9,346,026 | B2 | 5/2016 | Demel et al. |
| 10,821,256 | B2 | 11/2020 | Manigel et al. |

(Continued)

FOREIGN PATENT DOCUMENTS

| | | |
|---|---|---|
| DE | 102008057180 B3 | 4/2010 |
| DE | 102012008108 A1 | 10/2013 |
| DE | 102016001383 A1 | 8/2017 |

(Continued)

*Primary Examiner* — Margaret M Luarca
(74) *Attorney, Agent, or Firm* — McGlew and Tuttle, P.C.

(57) ABSTRACT

A device and to a process supply a patient-side coupling unit (9) with a gas mixture. The patient-side coupling unit is connectable to a patient (Pt). A first duct (K.1) guides a first gas component (air) from a first source (2) to a mixing point (8). A second source (20) provides a second gas component, which is guided to a front pressure inlet (V.3) of a pressure reducer (1). The pressure reducer provides the second gas component (O2) at a back pressure outlet (V.2). A time course of pressure at the back pressure outlet follows a time course of pressure at a reference point (11, 28.1) in the first duct. A second duct (K.2) guides the second gas component from the back pressure outlet to the mixing point. An inhalation duct (K.30) guides the gas mixture from the mixing point to the patient-side coupling unit.

20 Claims, 7 Drawing Sheets

(56) References Cited

U.S. PATENT DOCUMENTS

| | | | | |
|---|---|---|---|---|
| 2007/0125377 | A1* | 6/2007 | Heinonen | A61M 16/204 128/204.21 |
| 2018/0177961 | A1* | 6/2018 | Kagan | A61M 16/0883 |

FOREIGN PATENT DOCUMENTS

| | | | |
|---|---|---|---|
| DE | 102016009836 | A1 | 2/2018 |
| EP | 1795222 | B1 | 8/2010 |
| EP | 2425869 | A1 | 3/2012 |

* cited by examiner

Pt
9
100
3
4.1
8
Air + O2
K.30
30
28.1
Air
7.1
7.2
4.2
O2
28.2
ΔP
5.1
6.1
6.2
5.2
K.1
K.2
11
V.1
V.2
10
2
V.4
23
V.3
1
E
Luft
26
O2
21
W
20
O2

Pt
9
100
3
30
31
K.30
Air + $O_2$
4.1
8
27
28.1
A-Gas
7.1
Air + $CO_2$
7.2
4.2
$O_2$
28.2
25
6.1
ΔP
5.1
6.2
5.2
K.1
K.2
11
V.1
V.2
10
Air
32
2
V.4
V.3
23
1
26
21
W
20
$O_2$

SUPPLY DEVICE AND PROCESS FOR SUPPLYING A PATIENT-SIDE COUPLING UNIT WITH A GAS MIXTURE

CROSS REFERENCE TO RELATED APPLICATIONS

This application claims the benefit of priority under 35 U.S.C. § 119 of German Application 10 2021 132 927.2, filed Dec. 14, 2021, the entire contents of which are incorporated herein by reference.

TECHNICAL FIELD

The present invention pertains to a supply device and to a supply process for supplying a patient-side coupling unit with a gas mixture.

The present invention can be used, for example, for the artificial ventilation of a patient. A patient-side coupling unit, for example, a breathing mask, a catheter, or a tube, is arranged in or at the body of the patient. A gas mixture is delivered to a patient-side coupling unit in order to mechanically ventilate the patient. This gas mixture comprises oxygen. A ventilator preferably performs a sequence of ventilation strokes and delivers a quantity of the gas mixture to the patient-side coupling unit during each ventilation stroke.

BACKGROUND

It is possible to use breathing air as the gas mixture. It is often desired for the percentage of oxygen in the gas mixture that is delivered to the patient-side coupling unit to be higher than the percentage of oxygen in the breathing air and for it to follow a predefined time course (temporal profile), for example, to be constant over time. In order to achieve this object, a gas mixture comprising breathing air and pure oxygen is generated. The present invention can be used to generate such a gas mixture.

The ventilator 14 according to EP 2 425 869 A1 comprises a mixing device and a ventilation part. A medical gas, for example, oxygen or an anesthetic, is mixed with air in the mixing device. The medical gas is fed via a gas inlet B and is fed via a gas line 10. The air is fed via an air inlet A and is fed via an air line 11. A reducing valve 6, a safety valve 7, a controllable proportional valve 8 and a flow meter 9 are arranged in the gas line 10. A blower 1 and a nonreturn valve 2 are arranged in the air line 11. The ventilation part guides the gas mixture to a patient via a breathing gas line 12 as breathing gas. A flow sensor 3, a controllable proportional valve 4 and a pressure sensor 5 are arranged in the breathing gas line 12. A control unit 13 receives signals from the sensors 9, 3 and is capable of controlling all controllable valves 8, 4. The actuation is carried out with the control objective that the gas mixture in the breathing gas line 12 shall have a desired composition in terms of air and medical gas.

SUMMARY

A basic object of the present invention is to provide a supply device and a supply process, which are capable of supplying a patient-side coupling unit with a gas mixture comprising two gas components, wherein the time course of the volume flow or of the pressure of the gas mixture provided in a fluid connection to the patient-side coupling unit can be controlled in a relatively reliable manner.

This object is accomplished by a supply device having features according to the invention and by a supply process having features according to the invention. Advantageous embodiments are described herein. Advantageous embodiments of the supply device are, insofar as meaningful, also advantageous embodiments of the supply process according to the present invention and vice versa.

The supply device according to the present invention and the supply process according to the present invention are capable of supplying a patient-side coupling unit with a gas mixture. This gas mixture comprises a first gas component, especially air, and a second gas component, especially pure oxygen. It is also possible that one gas component is an anesthetic. The second gas component chemically differs from the first gas component. It is possible that both gas components comprise the same component, for example, both comprise oxygen.

The patient-side coupling unit is at least from time to time connected to a patient or can be connected to the patient. In particular, the patient-side coupling unit is arranged in or at the body of the patient or can be arranged there at least from time to time. A tube, a catheter and a breathing mask are examples of a patient-side coupling unit.

The term "duct" will be used below. A duct is defined as a component that is capable of guiding a fluid, especially a gas or gas mixture, along a predefined trajectory and ideally prevents the fluid from leaving this trajectory. A hose and a tube are examples of a duct. As a rule, the intended use of a duct is for fluid to be guided always or at least from time to time in one and the same direction through the duct but not in the opposite direction.

In addition, it will be stated below that a "fluid connection" is established between two components. This term is defined to mean that a fluid can flow from the one component to the other component, ideally without escaping into the surrounding area. It is possible that the two components are connected directly to one another. It is also possible that a distance occurs between the two components and a fluid guiding unit, for example, a hose and/or a duct connects the two components in the sense described above. It is possible that a fluid flows from time to time from the first component through the fluid connection to the second component and from time to time in the reverse direction from the second component to the first component through the fluid connection. The fluid connection may be established permanently or only temporarily.

Furthermore, the term "source" will hereinafter be used. In the context of the present invention a source may provide a fluid, especially a gas component of the gas mixture, continuously or at least from time to time. A source is especially a stationary supply port or a mobile source, for example, a container containing the fluid, especially a compressed air cylinder. It is also possible that a fluid delivery unit, for example, a pump or a blower of a ventilator, acts as a source for a fluid. It is possible that two different sources, especially a stationary source and a mobile source, are used for the same component.

The supply device according to the present invention comprises a first duct with a supply connection element, which acts as an inlet to the first duct. A fluid connection is at least from time to time established or can be established between the supply connection element and a first source. The first source is capable of providing the first gas component. The first duct is capable of guiding the first gas component from the supply connection element to a mixing point of the supply device. The pressure in the first duct may vary at one point of time along the first duct. As a rule, the pressure varies at a first point in the first duct over time.

The supply device further comprises a pressure reducer with a front (input, admission) pressure inlet and with a back (output, exit) pressure outlet. A pressure reducer is defined as a unit that receives at its front pressure inlet a gas, in this case the second gas component, with a front pressure and provides this gas with a back pressure at its back pressure outlet, the back pressure being lower than or equal to the front pressure. The pressure reducer keeps the back pressure below a pressure threshold wherein this pressure threshold may be defined by the construction of the pressure reducer. As a rule, the back pressure is variable over time, and the front pressure may also be variable over time. The pressure reducer guides at least from time to time the gas from the front pressure inlet through its interior to the back pressure outlet.

A fluid connection is at least from time to time established or can be established between the front pressure inlet and a second source. The second source is capable of providing the second gas component. Thanks to the fluid connection, the second gas component can flow from the second source to the front pressure inlet.

The pressure reducer is capable of providing the second gas component at its back pressure outlet. The pressure reducer is configured to provide the second gas component as follows: The time course of the pressure at the back pressure outlet follows the time course of the pressure at a reference point in the first duct. This reference point may be located in the supply connection element, be identical to the mixing point or be located between the connection element and the mixing point.

The feature that the time course of a physical variable B follows the time course of a physical variable A means the following: If A increases or decreases, B also increases or decreases, usually with a certain time delay. At least when A maintains the same value for a sufficiently long time period, i.e., A remains constant during this time period, B likewise assumes this value at least at the end of this time period.

The supply device further comprises a second duct. The back pressure outlet of the pressure reducer is pneumatically connected to the second duct and/or is in a fluid connection with the second duct. The second duct is capable of guiding the second gas component from the back pressure outlet of the pressure reducer to the mixing point.

The gas components, which are guided from the two ducts to the mixing point, are mixed together to form the gas mixture at the mixing point or are mixed by themselves to form the gas mixture.

In addition, the supply device comprises an inhalation duct, which leads from the mixing point to the patient-side coupling unit. The inhalation duct is capable of guiding the gas mixture, which has been or is being generated or emerged at the mixing point, to the patient-side coupling unit.

Consequently, the first duct and the second duct open according to the present invention into the mixing point, and the inhalation duct begins at the mixing point. In the simplest case, the mixing point is a purely mechanical component, which connects these three ducts to one another in the manner of a Y-piece. It is also possible that the mixing point is embodied by a gas mixer, which mixes the two gas components to form an ideally homogeneous gas mixture.

The present invention makes it possible to deliver a gas mixture comprising at least two gas components to the patient-side coupling unit and thereby to make the gas mixture available at the patient-side coupling unit for the artificial ventilation of a patient. Since the supply device is configured to compose the gas mixture from at least two gas components, the present invention makes it possible in many cases to provide a gas mixture which is tailored to the currently necessary artificial ventilation of the patient. In particular, pure oxygen may act as the second gas component, and the percentage of oxygen in the gas mixture can be set and changed when needed. The second gas component may also be an anesthetic, and the percentage of the anesthetic in the gas mixture can be set and changed.

Since a pressure reducer is arranged between the second source and the second duct, it is made possible for the second source to provide the second gas component with a higher pressure compared to the pressure with which the first source provides the first gas component. Since the pressure at the back pressure outlet and hence in the second duct follows the pressure prevailing at the reference point in the first duct, a great pressure difference is, as a rule, prevented from occurring at the mixing point, even if the two sources provide the two gas components with highly different pressures. Thanks to the pressure reducer the pressure with which the second source provides the second gas component can also be higher than the maximum allowable pressure of the gas mixture at the patient-side coupling unit.

These effects of the pressure reducer are especially advantageous in the case that the first source is a fluid delivery unit of a medical device and the second source is a stationary supply port or a pressurized container containing the second gas component. Examples of such a fluid delivery unit are a blower or a pump. The first source often supplies the first gas component with a pressure that is between 20 mbar and 100 mbar. The second source often delivers the second gas component with a pressure that is between 2 bar and 8 bar. It is possible, but thanks to the present invention not necessary, to reduce the pressure at the second source.

The pressure reducer supplies the second gas component at its back pressure outlet with a pressure that is lower than or at most equals the pressure at the front pressure inlet. According to the present invention, the pressure with which the second gas component is provided at the back pressure outlet follows the pressure of the first gas component at the reference point in the first duct. The pressure in the first duct is consequently the master and the pressure in the second duct is the slave.

This feature according to the present invention makes it easier to control the time course of the pressure or of the volume flow through the inhalation duct, i.e., downstream of the mixing point (closed-loop control). Such a control is often carried out as a closed-loop control with the control objective (control target) that the actual time course of the pressure or of the volume flow at the patient-side coupling unit should follow a predefined desired time course.

In addition, this feature makes it easier in some cases to control the time course of the pressure or of the volume flow upstream of the mixing point, i.e., in the first duct and/or in the second duct. In one embodiment the control objective of this control is to have the time course of the actual pressure or of the actual volume flow through the respective duct to follow a predefined desired time course. In another embodiment, the control [gain] objective is to have the percentage of at least one gas component in the gas mixture be in a predefined desired range. Both control objectives can or should be achieved in one embodiment. It is sufficient in some cases to control the pressure in the first duct. The pressure in the second duct will then follow the controlled pressure prevailing in the first duct.

Thanks to the present invention, the two gas components reach the mixing point with ideally the same pressure time course. In practice, the pressure in the second duct follows the pressure in the first duct with a time delay. The difference between the two pressures in the two ducts and hence the pressure difference at the mixing point remains relatively small at the mixing point at each time. Thanks to the present invention a reliable control of the volume flow or of the pressure or of the mixing ratio in the gas mixture is possible in many cases even when the desired time course predefines rapid changes of the pressure or of the volume flow or when the pressure with which a source provides a gas component is subject to variations over time. In many cases the present invention enables a control during which a control deviation is reduced rapidly. In addition, the present invention reduces the risk of a backlog caused by a great pressure difference between the two ducts at the mixing point. In general such a backlog is undesired.

To control the time course of the pressure in or of the volume flow through the inhalation duct, it is in many cases sufficient to control the time course of the pressure in or of the volume flow through the first duct. The time course of the pressure in or of the volume flow through the second duct follows, thanks to the present invention, the time course at the reference point in the first duct, without a control being necessary for the second duct as well.

It is not necessary, thanks to the pressure reducer according to the present invention, to control in an open-loop or closed-loop manner the pressure with which the second source provides the second gas component. It is rather possible for the second source to provide the second gas component with a constant pressure or with a pressure that changes independently from the pressure prevailing in the first duct. Nevertheless, the pressure in and/or the volume flow through the inhalation duct or the mixing ratio in the generated gas mixture can be controlled thanks to the present invention in a relatively reliable manner in many cases. The pressure reducer decouples the second source from the second duct and hence also from the first duct.

In one embodiment, an actuatable first valve is capable of changing the volume flow through the first duct or the pressure in the first duct, for example, by means of a variable cross-sectional area (proportional valve). A signal-processing control device (control unit) is capable of actuating this first valve. This control device carries out a first control (closed-loop control). During this first control the control device actuates the first valve depending on a signal of a first sensor.

In a first alternative of this embodiment, the control objective during the first control is to have the time course of the actual pressure in the first duct to follow a predefined desired pressure time course. The first sensor is capable of measuring an indicator of the pressure in the first duct.

In a second alternative of this embodiment, the control objective during the first control is to have the time course of the actual volume flow through the first duct to follow a predefined desired time course of the volume flow. The first sensor is capable of measuring an indicator of the volume flow through the first duct.

In a variant of this embodiment or in an alternative to this embodiment, the control device carries out a second control, which pertains to the second duct. A second valve is capable of changing the volume flow through the second duct and/or the pressure in the second duct. The control device actuates the second valve as a function of a signal of a second sensor.

In a first alternative of this variant, the control objective during the second control is to have the time course of the actual pressure in the second duct to follow a predefined desired time course of the pressure. The second sensor is capable of measuring an indicator of the pressure in the second duct.

In a second alternative of this variant, the control objective during the second control is to have the time course of the actual volume flow through the second duct to follow a predefined desired time course of the volume flow. The second sensor is capable of measuring an indicator of the volume flow through the second duct.

According to the present invention, the time course of the pressure at the back pressure outlet and hence in the second duct follows the time course of the pressure at the reference point in the first duct. In many cases this feature makes it easier to carry out the two controls just described. The same control algorithm can often be used for both controls.

It is also possible that the control device controls the volume flow through the first duct and/or through the second duct.

An alternative or additional control objective in one of these two embodiments may also apply for the percentage of the first gas component and/or for the percentage of the second gas component in the gas mixture, which is formed or generated or emerges at the mixing point, to follow a predefined time course, especially to be constant over time. Thanks to the present invention this control objective can also be achieved more easily.

In a preferred embodiment, the supply device comprises a pneumatic control line. On one side, the pneumatic control line is connected pneumatically to the pressure reducer, and on the other side it is connected to the first duct, specifically at a branch point. The branch point acts in this embodiment as a reference point in the first duct. The pneumatic control line establishes a fluid connection between the first duct, more precisely between the branch point, on the one hand, and the pressure reducer, on the other hand. The fluid connection leads to a pressure equalization between the two ends of the pneumatic control line. Thanks to the fluid connection, which is established by the pneumatic control line, the time course of the pressure in the pneumatic control line follows the time course of the pressure at the branch point. The pneumatic control line preferably brings about a pressure equalization between the pressure at the branch point and the pressure in an area of the pressure reducer, which is connected to the pneumatic control line. If the pressure at the branch point is constant over a sufficiently long time, the same pressure becomes established in this area of the pressure reducer as at the branch point thanks to the pressure equalization.

The pneumatic control line is pneumatically connected to the pressure reducer according to this embodiment. The pressure reducer is capable of causing the time course of the pressure at the back pressure outlet to follow the time course of the pressure in the pneumatic control line. On the whole, thereby it is achieved that the time course of the pressure at the back pressure outlet follows the time course of the pressure at the branch point.

The embodiment with the pneumatic control line eliminates in many cases the need for an electronic control device to actuate a component of the pressure reducer. Furthermore, it is possible but not necessary in many cases thanks to the embodiment to have a pressure sensor which measures the pressure at the reference point or at another measuring point in the first duct. The pressure reducer may rather be configured as a purely mechanical and pneumatic component. This makes possible in many cases an especially robust configuration of the pressure reducer. The pressure reducer does not need to be supplied with electrical energy in one embodiment. Even in the case that the pressure with which the second source provides the second gas component is several times higher than the pressure with which the first source provides the first gas component, the pneumatically operating pressure reducer is in many cases capable of providing the second gas component at its back pressure outlet without very strong forces occurring in the pressure reducer or without a very high pressure developing in the second duct.

In an implementation of the embodiment with the pneumatic control line, the pressure reducer has in its interior a front pressure chamber, a back pressure chamber and a control pressure chamber. The term "chamber" is defined as a space that is enclosed in a fluid-tight manner on all sides, without optional construction-related openings and usually inevitable slots and holes. It is possible that a housing of the pressure reducer forms at least one wall of such a chamber. The three chambers in the interior of the pressure reducer are separated from one another in a fluid-tight manner, aside from optional, construction-related openings and inevitable slots.

The front pressure chamber is at least from time to time connected via the front pressure inlet to the first source or it can be connected to the first source. The back pressure chamber is connected to the second duct in a fluid-tight manner via the back pressure outlet. As a rule, the front pressure is present in the front pressure chamber and the back pressure is present in the back pressure chamber. The control pressure chamber is connected to the pneumatic control line or is in a fluid connection with the pneumatic control line. The following is brought about by this connection: The pressure in the control pressure chamber follows the pressure in the pneumatic control line. The pressure reducer is configured such that the following is brought about: The time course of the pressure at the back pressure outlet follows the time course of the pressure in the control pressure chamber.

A preferred embodiment of the configuration with the three chambers will be described below. According to this embodiment, the pressure reducer comprises in its interior a partition wall and a movable closure. An opening is formed in the partition wall. The closure is capable of selectively releasing or closing the opening in the partition wall. The partition wall separates the front pressure chamber from the back pressure chamber. With the opening closed, the partition wall separates the two chambers from one another in a fluid-tight manner. Different pressures can therefore prevail in the two chambers without a pressure equalization taking place. With the opening released, a fluid connection is established between the front pressure chamber and the back pressure chamber, so that a pressure equalization takes place. As a rule, the pressure in the front pressure chamber is higher than the pressure in the back pressure chamber. With the fluid connection established with a pressure difference, the second gas component flows from the second source through the front pressure chamber and through the back pressure chamber into the second duct. With the opening released, a pressure equalization takes place to a certain degree between the two chambers. This fluid connection is interrupted or inhibited when the opening is closed, and the second duct is thereby separated from the second source. A high pressure in the second source will then not act on the back pressure chamber and consequently not on the second duct.

The pressure reducer is configured as follows: The closure releases the opening when a predefined criterion is met. This criterion depends on the pressure in the control pressure chamber and/or on the pressure in the back pressure chamber. For example, the criterion is met when the difference between the pressure in the control pressure chamber and the pressure in the back pressure chamber is above a construction-related and thereby predefined pressure difference threshold. Or else, the criterion is predefined when the pressure in the control pressure chamber is above a construction-related and thereby predefined pressure threshold. As long as the criterion is not met, the closure closes the opening. For example, a spring or other retaining element holds the closure in the closed position as long as the criterion is not met.

In a variant of the embodiment with the partition wall, the pressure reducer comprises, in addition to the partition wall, a movable wall. The movable wall may, in particular, be a rigid wall, which is movably arranged, or else a flexible wall, for example, a membrane. This movable or flexible wall separates the back pressure chamber from the control pressure chamber, doing so preferably in a fluid-tight manner. No opening is preferably formed in the movable or flexible wall, so that no fluid can flow from the first duct through the pressure reducer into the second duct, which is often undesirable.

Because this wall is movable, specifically relative to a housing of the pressure reducer, or flexible, the volume of the back pressure chamber and the volume of the control pressure chamber are variable. A pressure difference between the pressures in the two chambers brings about a movement of the movable or flexible wall, doing so such that the volume of one chamber is increased and the volume of the other chamber is accordingly reduced. As a result, a pressure equalization is brought about to a certain extent. This movable or flexible wall is in a functional connection (operative connection), preferably in a purely mechanical functional connection, with the closure for the opening in the partition wall. Thanks to this functional connection, a movement of the movable wall is transmitted to the closure. This movement causes the opening in the partition wall to be released or closed.

The embodiment just described with the pneumatic control line pneumatically causes the pressure at the back pressure outlet of the pressure reducer to follow the pressure at the reference point in the first duct. The alternative embodiment described below may be combined with the pneumatic control line or be used instead of a pneumatic control line. According to this alternative embodiment, the supply device comprises a pressure sensor and a signal-processing pressure-reducing control device. It is possible that the same control unit that actuates the movement of the first valve and/or the second valve is additionally used as the pressure-reducing control device.

The pressure sensor is capable of measuring an indicator of a pressure at a measuring point in the first duct. This measuring point preferably acts as the reference point. It is also possible that a distance occurs between the measuring point and the reference point and the pressure at the reference point is derived from the measured pressure at the measuring point and the distance between the measuring point and the reference point. Depending on measured values, the pressure sensor generates a signal for the pressure at the reference point. The pressure-reducing control device receives and processes this signal. Depending on the received and processed signal, the pressure-reducing control device is capable of causing the time course of the pressure at the back pressure outlet to follow the time course of the pressure at the reference point in the first duct.

In a variant of the embodiment with the pressure-reducing control device, the pressure reducer has in its interior two chambers, namely a front pressure chamber and a back pressure chamber. The front pressure chamber is at least from time to time connected or can be connected via the front pressure inlet to the first source. The back pressure chamber is connected to the second duct via the back pressure outlet. According to this variant, the pressure reducer comprises a pressure reducer actuator (final control element), for example, a pump or a piston-and-cylinder unit or a component with a lifting magnet or with a spring. The pressure-reducing control device is capable of actuating the pressures reducer actuator, doing so depending on a signal of the pressure sensor. The pressure reducer actuator is capable of changing the pressure in the back pressure chamber, preferably by the actuator causing the volume of the back pressure chamber to be changed. By actuating the pressure-reducing actuator, the pressure reducer control device is capable of automatically causing the time course of the pressure in the back pressure chamber to follow the time course of the pressure at the reference point in the first duct.

The embodiment with the pressure reducer and with the pressure reducer actuator causes in many cases the pressure in the back pressure chamber to follow the pressure in the first duct especially rapidly.

The embodiment with the pneumatic control line and the embodiment with the pressure reducer actuator may be combined with one another. On the one hand, redundancy is achieved thereby. On the other hand, the time course of the pressure at the back pressure outlet is caused to follow the time course of the pressure at the reference point more rapidly than if only the pneumatic control line or only the pressure reducer actuator were present.

In one embodiment of this variant, the pressure reducer comprises a partition wall between the front pressure chamber and the back pressure chamber, an opening in this partition wall and a closure. Possible embodiments and advantages of these elements were already described above as possible embodiments and advantages of the embodiment with the pneumatic control line and with the closable partition wall. The actuatable pressure reducer actuator is in a mechanical functional connection with the closure. The actuated pressure reducer actuator is capable of moving the closure and thereby of selectively releasing or closing the opening as desired.

In one embodiment, a movable or flexible wall is arranged in the interior of the pressure reducer. This wall is movable relative to another wall of the back pressure chamber, for example, to a housing of the pressure reducer, or is flexible. This movable or flexible wall preferably forms a wall of the back pressure chamber. A movement of the movable or flexible wall causes the volume of the back pressure chamber to change. As a result, the pressure in the back pressure chamber will be changed as well. The pressure reducer actuator is in a mechanical functional connection with the movable or flexible wall. By the pressure reducer actuator moving the movable or flexible wall, the pressure reducer actuator changes the pressure in the back pressure chamber and hence the pressure at the back pressure outlet of the pressure reducer.

This embodiment makes it possible in a relatively reliable manner for the pressure-reducing control device to control the pressure at the back pressure outlet. The control objective of this control is to have the pressure at the back pressure outlet to follow the time course of the pressure at the reference point. By the pressure-reducing control device actuating the pressure reducer actuator, the pressure-reducing control device changes the volume and hence the pressure in the back pressure chamber and hence at the back pressure outlet.

A control pressure chamber is additionally formed in the interior of the pressure reducer in one embodiment. The pressure reducer actuator is capable of changing the pressure in the control pressure chamber. The pressure, with which this pressure reducer provides the second gas component at its back pressure outlet, depends on the pressure in the control pressure chamber as follows: The greater the pressure in the control pressure chamber is, the greater is the pressure at the back pressure outlet.

In many cases the embodiment with the control pressure chamber makes it possible to arrange the pressure reducer actuator or at least any mechanical element of the pressure reducer actuator completely in the control pressure chamber. As a result, the or any other chamber of the pressure reducer is free from the pressure reducer actuator. The control pressure chamber protects the pressure reducer actuator from mechanical influences from outside up to a certain extent.

The present invention pertains, furthermore, to a supply system, which is capable of supplying a patient-side coupling unit with a gas mixture. The gas mixture comprises a first gas component and a second gas component. The supply system comprises a first source, a second source, and a supply device according to the present invention.

The first source is capable of providing the first gas component. The second source is capable of providing the second gas component. A fluid connection is established at least from time to time between the supply connection element of the first duct of the supply device and the first source. A fluid connection is likewise established at least from time to time between the front pressure inlet of the pressure reducer of the supply device and the second source.

In one embodiment, the second source provides the second gas component with a higher pressure compared to the pressure with which the first source provides the first gas component. For example, the second source is a stationary source, which is connected to a supply network of an infrastructure, or it comprises at least one pressurized cylinder. The first source is, for example, an inlet of a fluid delivery unit, especially of a blower or of a pump, wherein the fluid delivery unit belongs, for example, to a ventilator for artificial ventilation. The first source may also be another mobile source.

Furthermore, the present invention pertains to a system for artificial ventilation of a patient, wherein the patient is ventilated with a gas mixture comprising a first gas component and a second gas component. At least one of the two gas components, and optionally both gas components, is or contains oxygen. The gas mixture may comprise a third gas component, for example, an anesthetic.

The ventilation system comprises

- a fluid delivery unit, for example, a blower or a pump,
- a patient-side coupling unit as well as
- a supply device according to the present invention or a supply system according to the present invention.

The patient-side coupling unit is at least from time to time connected to a patient or can be connected to a patient, especially be arranged in or at the body of the patient.

A fluid connection is established during the artificial ventilation between a first source, which provides the first gas component, and the supply connection element. Furthermore, a fluid connection is established during the artificial ventilation between a second source for the second gas component and the front pressure inlet of the pressure reducer. The fluid delivery unit is capable of delivering the first gas component from the first source through the first duct to the mixing point. The second gas component flows from the second source to the mixing point, for example, based on a sufficiently high pressure in the second source or through same or through another fluid delivery unit. The time course of the pressure at the back pressure outlet of the pressure reducer follows the time course of the pressure at the reference point in the first duct.

The two gas components are mixed or emerge at the mixing point to form the gas mixture and they flow through the inhalation duct to the patient-side coupling unit.

The fluid delivery unit performs a sequence of ventilation strokes. During each ventilation stroke a quantity of the gas mixture, which is generated or is formed at the mixing point, is delivered through the inhalation duct to the patient-side coupling unit.

In one application, the patient performs an intrinsic breathing activity during the artificial ventilation, especially based on the patient's intrinsic spontaneous breathing or because the patient's respiratory muscles are externally stimulated or both. In this application the fluid delivery unit is preferably actuated such that each breath of the patient triggers a ventilation stroke of the fluid delivery unit and a ventilation stroke is performed only as a response to a breath. The artificial ventilation consequently supports the intrinsic breathing activity of the patient. The ventilation strokes, which are carried out by the fluid delivery unit, are ideally synchronized with the intrinsic breathing activity of the patient.

In one embodiment, the fluid delivery unit is in a fluid connection with the first duct and feeds the first gas component into the first duct. This first gas component is preferably ambient air or a gas, which is guided from the patient to the fluid delivery unit in a ventilation circuit. A stationary or mobile supply port feeds the second gas component into the second duct.

The present invention will be described below on the basis of an exemplary embodiment. The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which preferred embodiments of the invention are illustrated.

DESCRIPTION OF PREFERRED EMBODIMENTS

Figure 1:
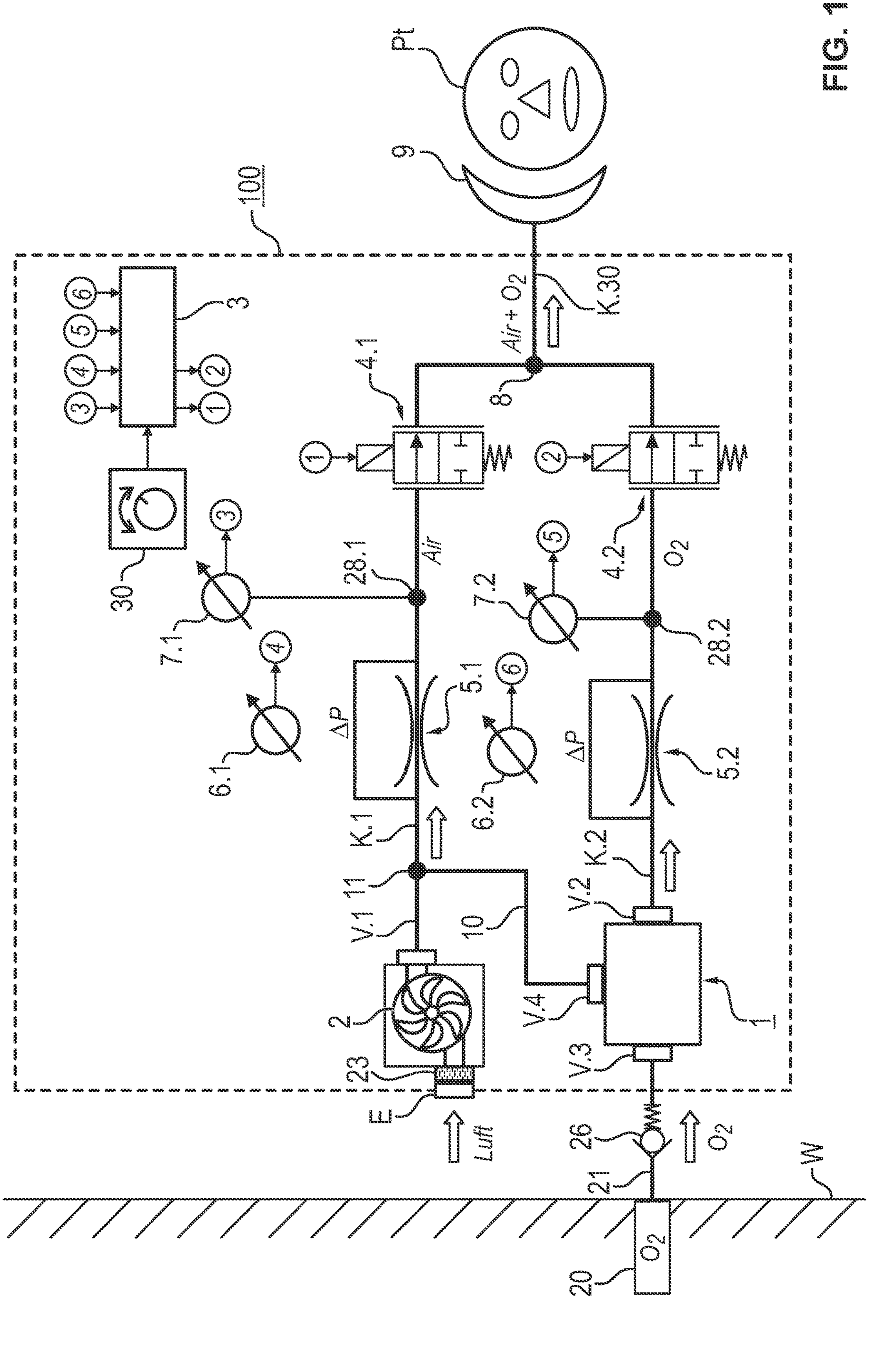
FIG. 1 is a schematic view showing how a patient is ventilated mechanically with a gas mixture comprising air and oxygen, wherein the two components are delivered by two ducts.

Referring to the drawings, the present invention is used in the exemplary embodiment to mechanically ventilate a patient Pt. A patient-side coupling unit 9, for example, a breathing mask or a tube or a catheter, is attached at or in the body of the patient Pt.

A ventilator 100, shown only schematically, performs a sequence of ventilation strokes and delivers a gas mixture to the patient-side coupling unit 9 and hence to the patient Pt during each ventilation stroke. This gas mixture contains a percentage (vol. %) of oxygen, this percentage having been predefined by a user. This percentage of oxygen may be higher than the percentage of oxygen in the breathing air. In order to increase the percentage of oxygen compared to breathing air, a gas mixture of breathing air and pure oxygen is generated in the exemplary embodiment. The gas mixture may additionally contain an anesthetic, so that the patient Pt is sedated or anesthetized.

FIG. 1 schematically shows a device for generating this gas mixture with a higher percentage of oxygen. The two components of the gas mixture, namely, air and pure oxygen, are provided in two ducts K.1 and K.2, a first duct K.1 providing the air and a second duct K.2 providing the oxygen, and the two ducts K.1 and K.2 being merged at a mixing point 8.

It is possible that a gas mixer mixes the two gas components to form the gas mixture. Such a gas mixer is described, for example, in DE 102008057180 B3 (corresponding to U.S. Pat. No. 8,356,596 B2 which is incorporated by reference), in DE 102012008108 A1 (corresponding to U.S. Pat. No. 9,346,026 B2 which is incorporated by reference), and in DE 102016001383 A1 (corresponding to U.S. Pat. No. 10,821,256 B2 which is incorporated by reference). A Y-piece is arranged at the mixing point 8 in the simplest case.

An inhalation duct K.30, for example, a hose for the inhalation and optionally a two-lumen hose with one lumen for the inhalation and one lumen for the exhalation, leads from this mixing point 8 to the patient-side coupling unit 9. This inhalation duct K.30 guides the mixture of air and pure oxygen to the patient-side coupling unit 9.

A user predefines a desired percentage of oxygen in the gas mixture. For example, the user sets the desired oxygen content manually by means of a rotary knob 30 shown schematically.

A blower 2 or another delivery unit of the ventilator 100 suctions ambient air through an inlet E of the ventilator 100 and feeds the suctioned air into the first duct K.1. A filter 23 is arranged between the inlet E and the blower 2. In the application according to FIG. 1, the delivery unit 2 acts as the source for the first gas component.

An inlet of the first duct K.1 in the form of a supply connection element V.1 is connected to a supply outlet of the blower 2. The pressure in the first duct K.1 ideally follows a predefined time course (temporal profile), and it is, for example, constant over time. The pressure in the first duct K.1 is above the maximum ventilation pressure in the exemplary embodiment, i.e., it is above the maximum pressure with which the gas mixture is delivered to the patient-side coupling unit 9 and farther into the lungs of the patient Pt, and it is preferably between 20 mbar and 100 mbar.

Figure 3:
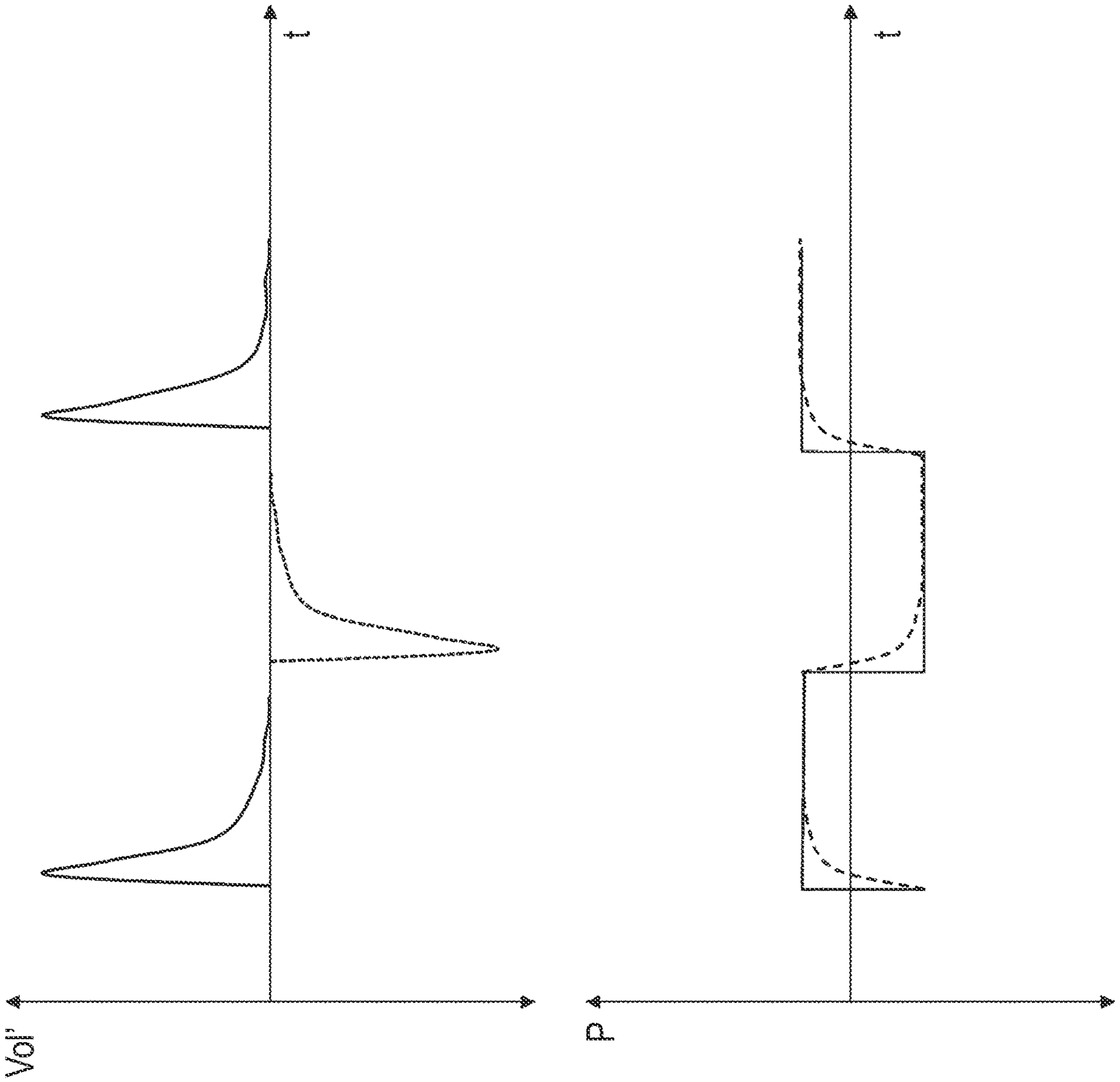
FIG. 3 is a schematic view showing the time course of the volume flow and that of the pressure of the gas mixture that is flowing to the patient.

The volume flow, i.e., the flow of gas per unit of time, through the first duct K.1 downstream of the delivery unit 2 and/or the pressure in the first duct K.1 shall follow each a respective predefined time course. FIG. 3 shows an exemplary required time course of the volume flow (Vol') at the top and an exemplary required time course of the pressure (P) at the bottom. Values over the x axis mean a flow of the gas mixture towards the patient Pt (inhalation) and values under this axis mean a flow away from the patient Pt (exhalation).

A signal-processing control device 3 carries out a control, wherein the actual volume flow is the controlled variable. The predefined time course of the volume flow is the command variable, cf. FIG. 1 and FIG. 2. The control device 3 actuates a proportional valve 4.1 and changes thereby the volume flow through the first duct K.1 downstream of the proportional valve 4.1 to the mixing point 8.

A pneumatic resistance 5.1, for example, a narrowing, is arranged in the first duct K.1. A volume flow sensor 6.1 measures the difference ΔP between the pressure upstream and the pressure downstream of the pneumatic resistance 5.1 and derives an indicator of the actual volume flow through the first duct K.1 from the pressure difference. In addition, a pressure sensor 7,1 measures the actual pressure in the first duct K.1 at a measuring point 28.1 downstream of the pneumatic resistance 5.1. The control device 3 receives a signal each from the two sensors 6.1 and 7.1.

The second duct K.2 receives pure oxygen (O2) from a supply line 21, which is in connection with a supply port 20. This supply port 20 is arranged in the example shown stationarily in a wall W and belongs to a stationary supply system of a hospital infrastructure. It is also possible that the second duct K.2 receives pure oxygen from at least one pressurized cylinder. The supply port 20 provides the pure oxygen with a pressure that is between 2 bar and 8 bar. An optional nonreturn valve 26 in the supply line 21 prevents pure oxygen from being pressed back into the supply port 20 and then into the hospital infrastructure.

A pneumatic pressure reducer 1 comprises a front pressure inlet V.3 and a back pressure outlet V.2. The front pressure inlet V.3 is connected to the supply line 21, and the back pressure outlet V.2 is connected to the second duct K.2. The pressure reducer 1 reduces the pressure from the supply port 20 with the aim of having the pressure at the back pressure outlet V.2 of the pressure reducer 1 follow the pressure, which is variable over time, at a reference point 11, 28.1, which will be described below. As a result, the pressure at the back pressure outlet V.2 follows the pressure at the supply connection element V.1 and hence the pressure at the supply outlet of the blower 2. How this goal is achieved will be described in more detail below.

A pneumatic resistance 5.2, a volume flow sensor 6.2, a pressure sensor 7.2 and a proportional valve 4.2 are arranged in the second duct K.2. These components operate like the corresponding components in the first duct K.1. The pressure sensor 7.2 measures at a measuring point 28.2 an indicator of the pressure in the second duct K.2. The control device 3 controls in the exemplary embodiment the proportional valve 4.2 with the control objective of having the actual volume flow through the second duct K.2 to follow a predefined time course.

Figure 2:
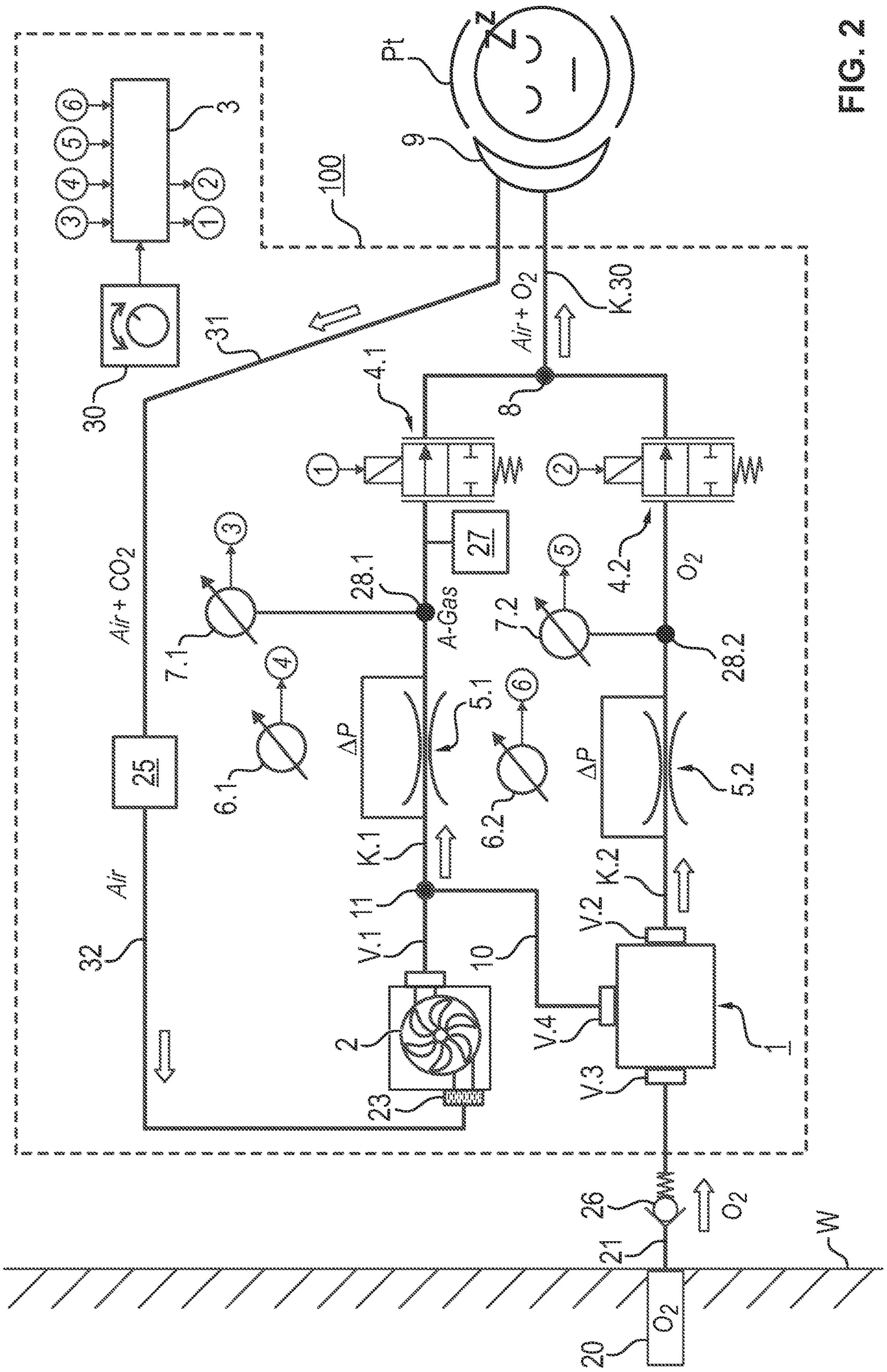
FIG. 2 is a schematic view showing a ventilation circuit, in which a patient is supplied with a mixture of air, oxygen and an anesthetic and is anesthetized with a mixture of air, oxygen and an anesthetic.

FIG. 2 shows another application of the present invention, in which the patient Pt is not only ventilated mechanically, but is additionally also sedated or anesthetized. Identical reference numbers have the same meanings as in FIG. 1.

The embodiment according to FIG. 2 has the following additional components:

- an anesthetic evaporator 27, which generates gaseous anesthetic,
- an exhalation fluid connection with a first section 31 and with a second section 32, and
- an absorber 25 for CO2 and anesthetic.

The gaseous anesthetic, which is generated by the anesthetic evaporator 27, is fed into the gas mixture, which is guided through the inhalation duct K.30 to the patient-side coupling unit 9 and is inhaled by the patient Pt. The anesthetic is fed in the example shown into the first duct K.1 and it flows into this to the mixing point 8. It is also possible that it is fed into the second duct K.2 or into the inhalation duct K.30.

The air exhaled by the patient Pt often still contains anesthetic. This anesthetic shall not escape into the surrounding area. A closed ventilation circuit is therefore formed. The exhalation fluid connection 31, 32 leads from the patient-side coupling unit 9 back to the blower 2. The blower 2 maintains a flow of gas through this closed ventilation circuit. The first section 31 leads from the patient-side coupling unit to the CO2 absorber 25. This CO2 absorber 25 absorbs carbon dioxide and optionally also anesthetic from the exhaled air. The second section 32 guides the exhaled air, from which the carbon dioxide and optionally the anesthetic had been absorbed, to the filter 23 and from there to the blower 2.

The absorber 25 acts in this embodiment as the source for the first gas component (air), which enters into the first duct K.1.

As was already described, a gas mixture is delivered from the mixing point 8 to the patient-side coupling unit 9. The actual volume flow of this gas mixture downstream of the mixing point 8 shall follow a predefined time course. In addition, a required percentage of oxygen is predefined, preferably as vol. %. This oxygen content may be constant over time or variable over time. The predefined time course of the volume flow to the patient-side coupling unit 9, the required percentage of oxygen in the gas mixture as well as the known percentage of oxygen in the air result in a desired time course of the volume flow through the first duct K.1 and in a desired time course of the volume flow through the second duct K.2. The control device 3 or a higher-level control device calculates these two desired time courses for the two ducts K.1 and K.2, and the control device 3 actuates the two proportional valves 4.1 and 4.2 as a function of these two desired time courses. The control device 3 consequently carries out two controls of the volume flow, namely, one in the first duct K.1 and one in the second duct K.2. The same control algorithm can be used in many cases to actuate the two proportional valves 4.1 and 4.2. This is possible especially because the same pressure is present at the supply outlet of the blower 2 and at the back pressure outlet V.2 of the pressure reducer 1. This is brought about by the pneumatic or electronic control (open-loop control) or control (closed-loop control) described below.

Figure 4:
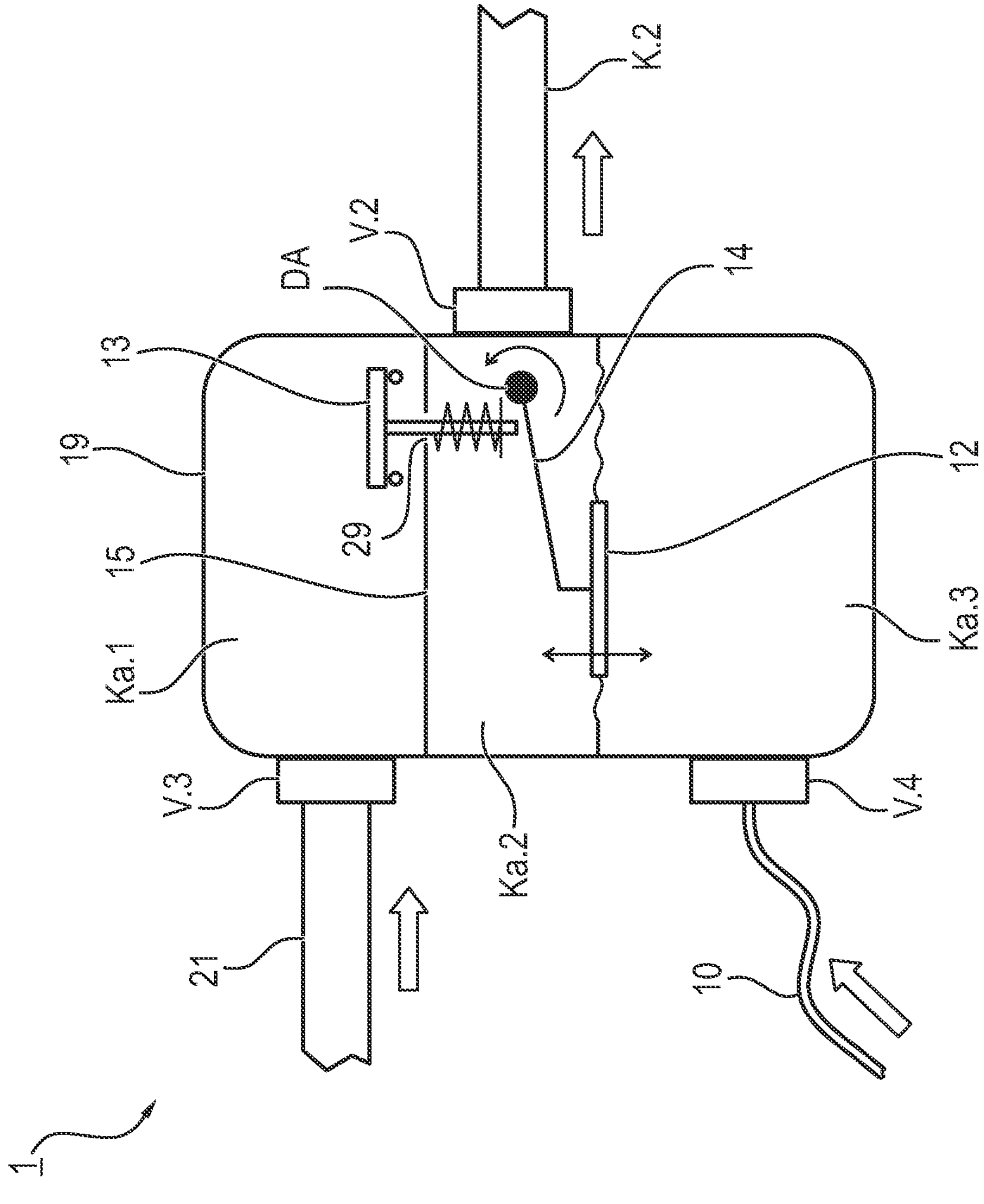
FIG. 4 is a schematic view showing a purely pneumatic pressure reducer.

FIG. 1 and FIG. 4 illustrate a pneumatic control of the pressure reducer 1. A pneumatic control line 10 leads from a branch point 11 in the first duct K.1 to a control pressure inlet V.4 of the pressure reducer 1. This control pressure inlet V.4 is needed for the pneumatic control, but not for the electronic control or control described below. The pneumatic control line 10 is preferably configured as a flexible hose, but it may also be a rigid tube. The branch point 11 is arranged downstream of the blower 2 and upstream of the proportional valve 4.1; it also begins upstream of the pneumatic resistance 5.1 in the embodiment shown, and this branch point 11 acts as the reference point in one embodiment.

Thanks to the pneumatic control line 10, the same pressure is always present at the control pressure inlet V.4 of the pressure reducer 1, aside from inevitable time delays and leaks, as in the first duct K.1, and there in the section between the blower 2 and the proportional valve 4.1 and especially as at the reference point (branch point 11). This pressure in the first duct K.1, which is variable over time, acts as a control pressure and hence as a master and the pressure in the inlet of the second duct K.2 follows this control pressure, which is variable over time, as a slave.

FIG. 4 shows an exemplary embodiment of a pneumatically operating pressure reducer 1. The front pressure inlet V.3 of the pressure reducer 1 is connected to the supply line 21. The control pressure inlet V.4 is connected to the pneumatic control line 10. The second duct K.2 is connected to the pneumatic control line 10. The second duct K.2 begins in the back pressure outlet V.2 of the pressure reducer 1.

A rigid housing 19 encloses the interior of the pressure reducer 1. Three chambers, namely

- a front pressure chamber Ka.1, which is in a fluid connection with the supply line 21 via the front pressure inlet V.3,
- a back pressure chamber Ka.2, which is in a fluid connection with the second duct K.2 via the back pressure outlet V.2, as well as
- a control pressure chamber Ka.3, which is in a fluid connection with the pneumatic control line 10 via the control pressure inlet V.4, are formed in this interior.

A partition wall 15 in the pressure reducer 1 separates the back pressure chamber Ka.2 from the front pressure chamber Ka.1. The partition wall 15 is preferably rigid. An opening 29 is preferably formed in the partition wall 15. A spring-loaded closure 13 is movable linearly relative to the partition wall 15 in two opposite directions (vertically upwards and downwards in FIG. 4) and can release or close this opening 29.

A movable wall 12 is fastened on the inside to the housing of the pressure reducer 1 and it separates the control pressure chamber Ka.3 from the back pressure chamber Ka.2. The movable wall 12 has the shape of a flexible membrane in the exemplary embodiment. The membrane 12 comprises in one embodiment a fixed plate arranged in a centered manner. The movable wall 12 may also have the form of a rigid plate, which is displaceable vertically in both directions relative to the housing 19. The movable wall 12 preferably separates the two chambers Ka.2 and Ka.3 from one another in a fluid-tight manner, aside from inevitable leaks.

The just described construction of the pressure reducer 1 causes the second gas component, here oxygen, to be contained in the front pressure chamber Ka.1 and in the back pressure chamber Ka.2, and the first gas component, here air, to be contained in the control pressure chamber Ka.3. The movable wall 12 prevents these two gas components from mixing with one another in the pressure reducer 1. In a state in which the closure 13 releases the opening 29, the two chambers Ka.1 and Ka.2 are in a fluid connection with one another, and a pressure equalization can take place. With the opening 29 closed, the partition wall 15 interrupts this fluid connection and prevents a pressure equalization.

A lever 14 is rotatable about an axis of rotation and it lies at the top on the movable wall 12, optionally at the top on the fixed plate of the membrane. The closure 13 lies at the top on the lever 14. As can be seen in FIG. 4, a short lever arm is formed between the axis of rotation DA and the contact point of the closure 13 as well as a long lever arm is formed between the axis of rotation DA and the contact point of the lever 14 on the movable wall 12. As a result, the movable wall 12 is in a functional connection with the closure 13 and can apply a strong force to the closure 13.

The same pressure prevails in the front pressure chamber Ka.1 as in the supply line 21, i.e., a front pressure that is preferably between 2 bar and 8 bar and is therefore several times higher than the pressure in the two ducts K.1 and K.2. The same pressure prevails in the control pressure chamber Ka.3 as in the pneumatic control line 10 and consequently ideally also the same pressure prevails there as in the first duct K.1 and there in the section between the blower 2 and the proportional valve 4.1. The same pressure with which the second duct K.2 provides pure oxygen is generated in the back pressure chamber Ka.2.

Thanks to the movable wall 12, the same pressure always becomes established in the two chambers Ka.2 and Ka.3 in case of a variable control pressure (pressure in the first duct K.1) as well. After a change in the control pressure, i.e., in the pressure in the control pressure chamber Ka.3, there is, as a rule, a transient phase before the pressures become equal again. Depending on the position of the movable wall 12, the closure 13 therefore opens or closes the opening 29 in the partition wall 15 and thus makes possible or prevents the flow of pure oxygen from the supply line 21 through the pressure reducer 1 into the second duct K.2. In case of a sufficiently high pressure in the back pressure chamber Ka.2, the movable wall 12 brings about closing of the opening 29 by the closure 13 by means of the functional connection (lever 14).

The blower 2 ideally generates a constant pressure, doing so independently from the volume flow. This constant pressure is therefore likewise present ideally at the outlet of the pressure reducer 1. The generated pressure decreases in practice with increasing volume flow.

Figure 5:
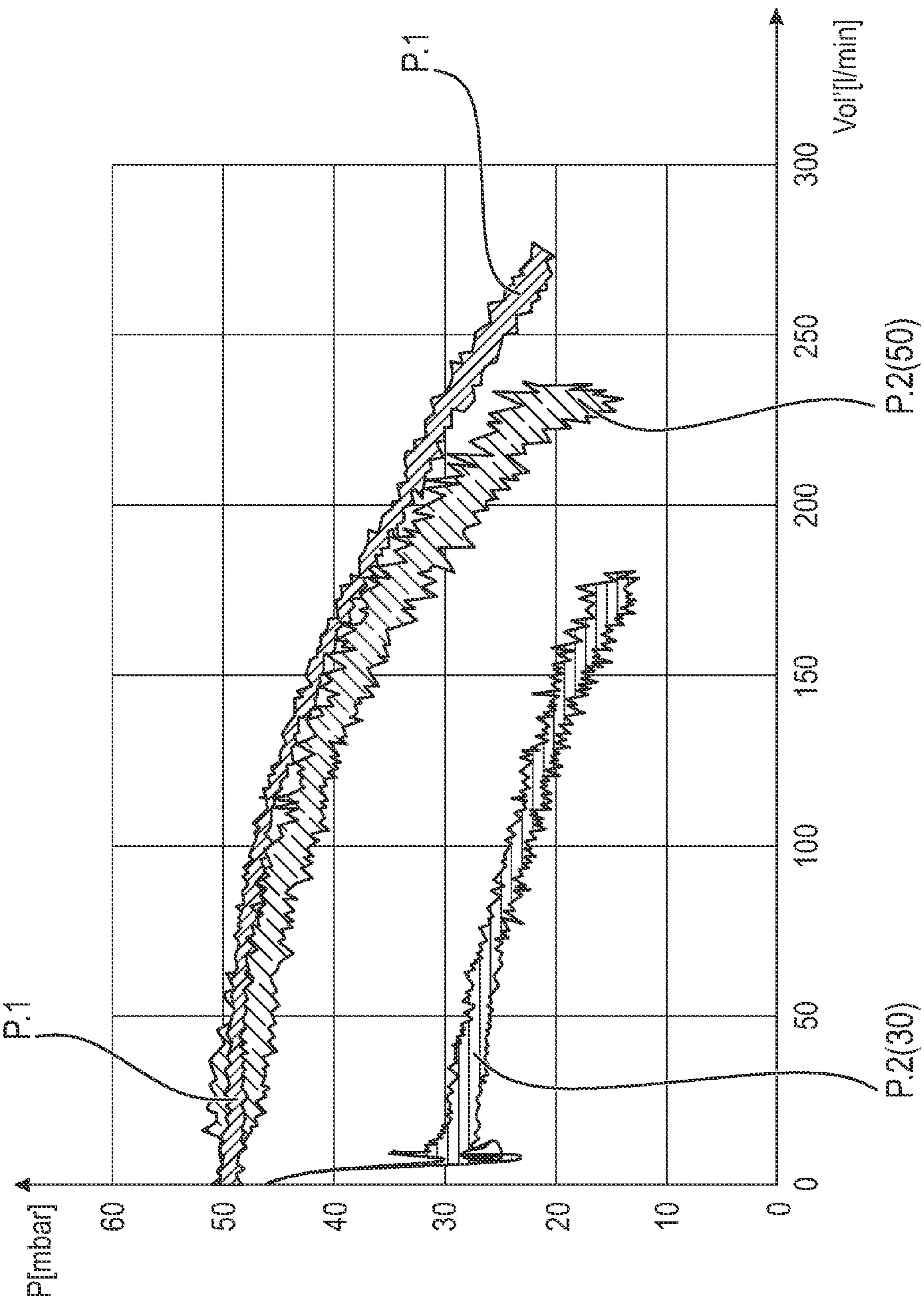
FIG. 5 is a schematic view showing an exemplary dependence of the back pressure on the volume flow.

FIG. 5 shows this situation as an example, the volume flow Vol' in [L/min] being plotted on the x axis and the generated back pressure P in [mbar] on the y axis. The designation "back pressure" relates to the outlet of the blower 2. The time course P.2(50) shows the time course of the actual pressure P, which is generated by the blower 2, depending on the volume flow Vol' in a situation in which the blower 2 shall generate a pressure of 50 mbar. The time course P.2(30) shows the actual pressure at a desired pressure of 30 mbar. The time course P.1 shows the actual pressure at the back pressure outlet V.2 of the pressure reducer 1. It can be seen that despite the dependence on the volume flow, the pressure at the outlet of the pressure reducer 1 is closely correlated with the control pressure (back pressure of the blower 2).

Figure 6:
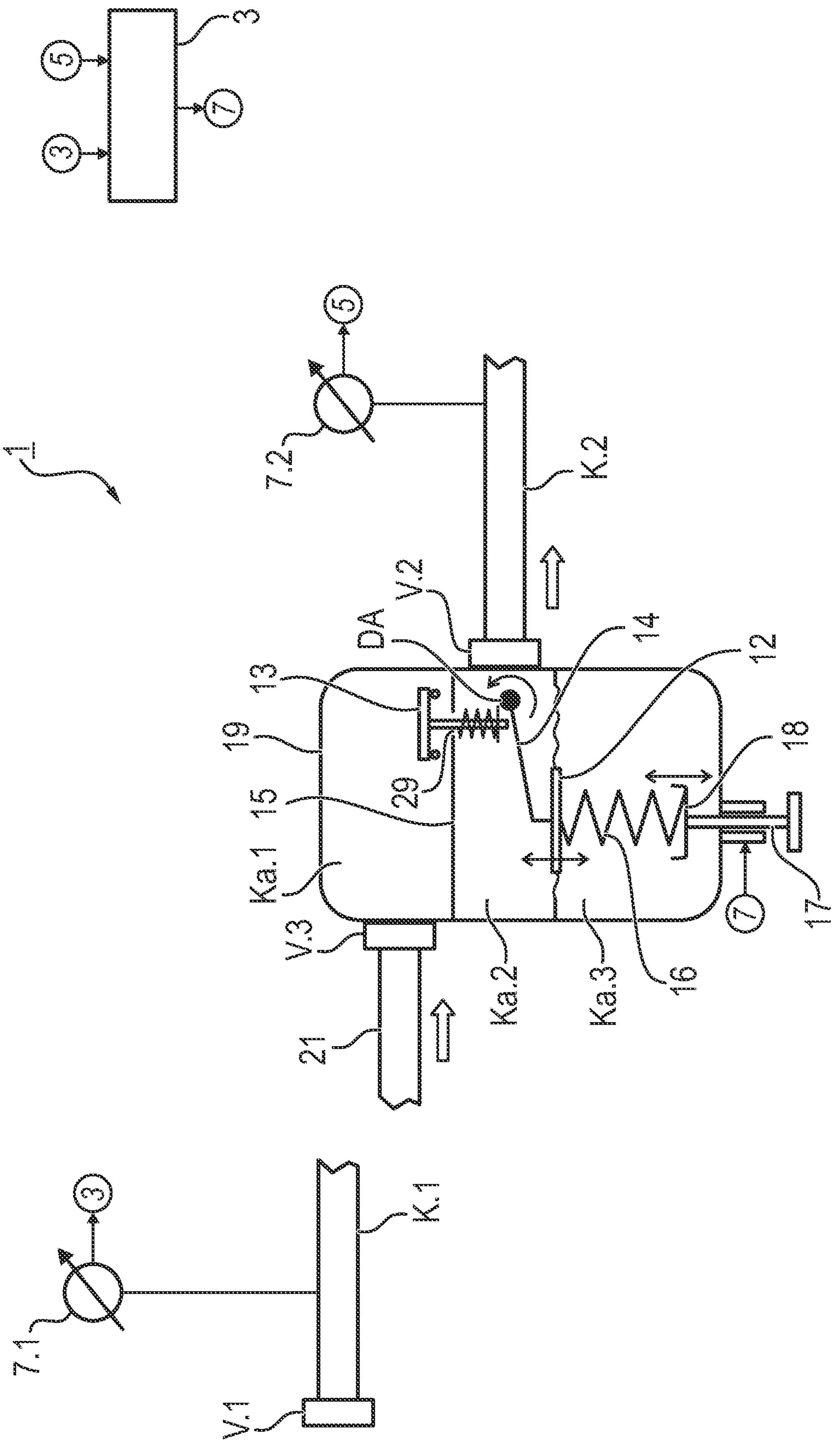
FIG. 6 is a schematic view showing an actuated pressure reducer with a control pressure chamber.
Figure 7:
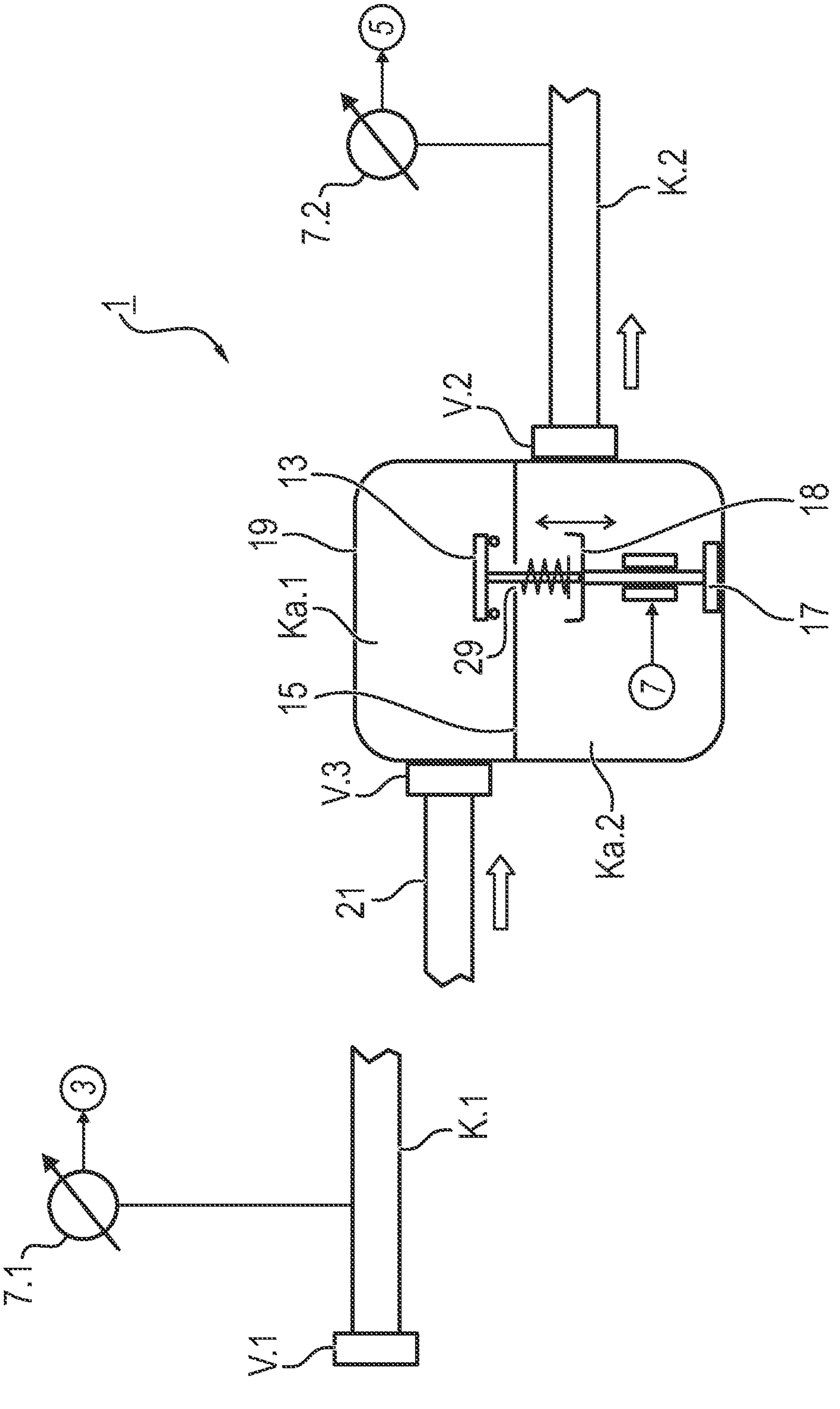
FIG. 7 is a schematic view showing an actuated pressure reducer without a control pressure chamber.

FIG. 6 and FIG. 7 show two alternative embodiments of the pressure reducer 1. Identical reference numbers have the same meanings as in FIG. 1 and in FIG. 4. The measuring point 28.1, at which the pressure sensor 7.1 measures the pressure, is used as the reference point.

The two alternative embodiments eliminate the need for a pneumatic control line 10 from the first duct K.1 to the pressure reducer 1 as well as for a pneumatic control pressure inlet V.4. Identical reference numbers have the same meanings as in FIG. 4. In the two alternative embodiments, the pressure reducer 1 has only one inlet, namely, the front pressure inlet V.3, which connects, in turn, the front chamber Ka.1 to the supply line 21.

The embodiment according to FIG. 6 will be described first. The pressure acts likewise from one side on the movable wall 12 in the back pressure chamber Ka.2, and the force of a spring 16 acts from the other side in the control pressure chamber Ka.3. The spring 16 is connected on the one side to the movable wall 12 and on the other side to a mechanical connection element 18 and it seeks to expand. An actuated control pressure actuator 17, for example, a pump or a piston-and-cylinder unit, is supported at the housing 19 of the pressure reducer 1 and acts from one side on the connection element 18. The control pressure actuator 17 is capable of increasing and decreasing the distance between the connection element 18 and the lower wall of the housing 19 and thereby also the force of the spring 16. The closer the connection element 18 is to the movable wall 12, the stronger is the spring force of the spring 16.

The control device 3 receives a respective signal each from the two pressure sensors 7.1 and 7.2, cf. FIG. 1, and controls the control pressure actuator 17 such that the pressure in the control pressure chamber Ka.3 and hence the pressure in the second duct K.2 follows the pressure in the first duct K.1 downstream of the blower 2.

The pressure reducer 1 according to FIG. 7 comprises no control pressure chamber and no movable wall. The control pressure actuator 17 is located in the back pressure chamber Ka.2 and is mechanically connected to the closure 13 via the connection element 18. The control pressure actuator 17 is capable of directly moving the closure 13 in two opposite, vertical directions and is thereby able to move the closure 13 optionally into a released position or into a closed position.

The embodiments according to FIG. 4 and according to FIG. 6 or FIG. 7 of the pressure reducer 1 may be combined with one another. According to this combination, the pressure reducer 1 consequently has both the control pressure inlet V.4 and the spring 16, the control pressure actuator 17 and the connection element 18. The supply device is preferably configured in this combination as it is shown in FIG. 1. The actuated control pressure actuator 17 and the spring 16 can compensate differences between the pressure in the back pressure chamber Ka.2 and the pressure in the first duct K.1 to a certain extent.

While specific embodiments of the invention have been shown and described in detail to illustrate the application of the principles of the invention, it will be understood that the invention may be embodied otherwise without departing from such principles.

| List of Reference Characters | |
|---|---|
| 1 | Pneumatic pressure reducer between the supply line 21 and the second duct K.2; it comprises the back pressure outlet V.2, the front pressure inlet V.3 and the optional control pressure inlet V.4 |
| 2 | Blower of the ventilator 100; it comprises the inlet E; it is connected via a supply outlet to the first duct K.1, acts as the first source in one embodiment |
| 3 | Signal-processing control device; it receives signals from the sensors 6.1, 6.2, 7.1, 7.2 and actuates the proportional valves 4.1 and 4.2 and in one embodiment the control pressure actuator 17 |
| 4.1 | Proportional valve in the first duct K.1; it is capable of changing the volume flow through the first duct K.1; it is actuated by the control device 3 |
| 4.2 | Proportional valve in the second duct K.2; it is capable of changing the volume flow through the second duct K.2; it is actuated by the control device 3 |
| 5.1 | Pneumatic resistance in the first duct K.1 |
| 5.2 | Pneumatic resistance in the second duct K.2 |
| 6.1 | Volume flow sensor; it measures the pressure difference ΔP upstream and downstream of the pneumatic resistance 5.1 and derives the volume flow through the first duct K.1 |

-continued

| List of Reference Characters | |
|---|---|
| 6.2 | Volume flow sensor; it measures the pressure difference ΔP upstream and downstream of the pneumatic resistance 5.2 and derives the volume flow through the second duct K.2 |
| 7.1 | Pressure sensor; it measures at the measuring point 28.1 an indicator of the pressure in the first duct K.1 |
| 7.2 | Pressure sensor; it measures at the measuring point 28.2 an indicator of the pressure in the second duct K.2 |
| 8 | Mixing point, at which the two ducts K.1 and K.2 open and at which the inhalation duct K.30 begins |
| 9 | Patient-side coupling unit, connected to the mixing point 8 via the inhalation duct K.30 |
| 10 | Pneumatic control line; it leads from the branch point 11 to the control pressure chamber Ka.3 in the pressure reducer 12; it belongs to the pressure-reducing control device |
| 11 | Branch point in the first duct K.1, in which the control line 10 begins; it acts as the reference point in one embodiment |
| 12 | Movable wall in the form of a membrane in the pressure reducer 1; it separates the chambers Ka.2 and Ka.3 from one another in a fluid-tight manner |
| 13 | Closure, which optionally closes or opens the connection in the partition wall 15 between the two chambers Ka.1 and Ka.2; it is in a functional connection with the movable wall 12 via the lever 14 |
| 14 | Lever; it establishes a mechanical functional connection between the movable wall 12 and the closure 13; it is rotatable about the axis of rotation DA |
| 15 | Rigid partition wall in the pressure reducer 1, which wall separates the two chambers Ka.1 and Ka.2 from one another; it has an opening 29, which can be closed by the closure 13 |
| 16 | Spring; it is connected to the movable wall 12 and to the connection element 18; it belongs to the pressure reducer actuator |
| 17 | Control pressure actuator, which moves the connection element 18 and thus changes the force of the spring 16; it is actuated by the control device 3; it belongs to the pressure reducer actuator |
| 18 | Mechanical connection element between the control pressure actuator 17 and the spring 16 |
| 19 | Rigid housing of the pressure reducer 1; it encloses the three chambers Ka.1, Ka.2, Ka.3 |
| 20 | Supply port in the wall W for pure oxygen; it acts as the second source |
| 21 | Supply line; it leads from the supply port 20 to the front pressure inlet V.3; it connects the supply port 20 to the front pressure chamber Ka.1 in the pressure reducer 1 |
| 23 | Filter behind the inlet E |
| 25 | CO2 absorber; it acts as the first source in one embodiment |
| 26 | Nonreturn valve in the supply line 21 |
| 27 | Anesthetic evaporator; it generates gaseous anesthetic and feeds same into the first duct K.1 |
| 28.1 | Measuring point in the first duct K.1, at which the pressure sensor 7.1 measures the pressure in the first duct K.1; it acts as the reference point in one embodiment |
| 28.2 | Measuring point in the second duct K.2, at which the pressure sensor 7.2 measures the pressure in the second duct K.2 |
| 29 | Opening in the partition wall 15; it is optionally released or closed by the closure 13 |
| 30 | Rotary knob, which a user can rotate in order to predefine the desired percentage of oxygen in the gas mixture, which is delivered to the patient-side coupling unit 9 |
| 31 | First section of the exhalation fluid connection; it guides the exhaled air from the patient-side coupling unit 9 to the CO2 absorber 25 |
| 32 | Second section of the exhalation fluid connection; it guides the exhaled air freed from CO2 from the CO2 absorber 25 to the blower 2 |

-continued

| List of Reference Characters | |
|---|---|
| 100 | Ventilator; it generates a gas mixture from breathing air and pure oxygen; it ventilates the patient Pt mechanically; it comprises the supply device according to the present invention |
| DA | Axis of rotation, about which the lever 14 can be rotated |
| E | Inlet for ambient air |
| K.1 | First duct; it provides breathing air; it is in a fluid connection with the blower; it opens into the mixing point 8 |
| K.2 | Second duct; it provides pure oxygen; it is in a fluid connection with the back pressure chamber Ka.2 in the pressure reducer 1; it opens into the mixing point 8 |
| K.30 | Inhalation duct; it guides the gas mixture from the mixing point 8 to the patient-side coupling unit 9 |
| Ka.1 | Front pressure chamber in the pressure reducer 1, connected via the front pressure inlet V.3 to the supply line 21 |
| Ka.2 | Back pressure chamber in the pressure reducer 1, connected via the back pressure outlet V.2 to the second duct K.2 |
| Ka.3 | Control pressure chamber in the pressure reducer 1, connected in one embodiment via the control pressure inlet V.4 to the control line 10; it contains in another embodiment the spring 16 and the connection element 18 |
| P | Pressure, especially in the inhalation duct K.30 |
| P.1 | Time course of the pressure at the back pressure outlet V.2 |
| P.2 | Time course of the pressure at the supply connection element V.1 |
| P.2(30) | Time course at a desired pressure of 30 mbar |
| P.2(50) | Time course at a desired pressure of 50 mbar |
| Pt | Patient; the patient is ventilated mechanically (artificially) by the ventilator 100; the patient carries the patient-side coupling unit 9 |
| V.1 | Supply connection element of the first duct K.1, connected to a supply outlet of the blower 2 |
| V.2 | Back pressure outlet of the pressure reducer 1, connected to the second duct K.2 |
| V.3 | Front pressure inlet of the pressure reducer 1, connected to the supply line 21 |
| V.4 | Optional control pressure inlet of the pressure reducer 1, connected to the control line 10 |
| Vol' | Volume flow through the first duct K.1 |
| W | Wall; it has the supply port 20 for pure oxygen |

What is claimed is:

1. A supply device for supplying a patient-side coupling unit with a gas mixture, the gas mixture comprising a first gas component and a second gas component, wherein the patient-side coupling unit is connected or connectable to a patient, the supply device comprising:

a first duct with a supply connection element configured to establish a fluid connection with a first source for the first gas component;

a second duct;

a mixing point;

an inhalation duct;

a pressure reducer with a front pressure inlet configured to establish a fluid connection with a second source for the second gas component and with a back pressure outlet connected to the second duct;

a first valve configured to change a volume flow through the first duct or a pressure in the first duct or both the volume flow through the first duct and the pressure in the first duct;

a first sensor configured to measure an indicator of pressure in the first duct or configured to measure an indicator of volume flow through the first duct; and a signal-processing control device configured to carry out a first closed-loop control to actuate the first valve during the first control as a function of measured values of the first sensor and based on a first control objective;

wherein the first duct is configured to guide the first gas component from the supply connection element to the mixing point, wherein the second duct is configured to guide the second gas component from the back pressure outlet to the mixing point, wherein the pressure reducer is configured to provide the second gas component such that a time course of pressure at the back pressure outlet follows a time course of pressure at a reference point in the first duct, wherein the inhalation duct is configured to guide a gas mixture generated or emerged at the mixing point to the patient-side coupling unit, and wherein:

the first sensor is configured to measure an indicator of pressure, and the first control objective is the actual time course of pressure in the first duct to follow a predefined desired pressure time course; or the first sensor is configured to measure an indicator of volume flow, and the first control objective is the actual time course of volume flow through the first duct to follow a predefined desired volume flow time course.

2. The supply device in accordance with claim 1, further comprising:

a second valve configured to change a volume flow through the second duct or a pressure in the second duct or both the volume flow through the second duct and the pressure in the second duct;

a second sensor configured to measure an indicator of pressure in the second duct or configured to measure an indicator of volume flow through the second duct; and a signal-processing control device configured to carry out a second closed-loop control to actuate the second valve during the second control as a function of measured values of the second sensor and based on a second control objective, wherein:

the second sensor is configured to measure an indicator of pressure, and the second control objective is the actual time course of pressure in the second duct to follow a predefined desired pressure time course; or the second sensor is configured to measure an indicator of volume flow and the second control objective is the actual time course of volume flow through the second duct to follow a predefined desired volume flow time course.

3. The supply device in accordance with claim 1, further comprising:

a second valve configured to change a volume flow through the second duct or a pressure in the second duct or both the volume flow through the second duct and the pressure in the second duct; and a second sensor configured to measure an indicator of pressure in the second duct or configured to measure an indicator of volume flow through the second duct; and a signal-processing control device configured to carry out a second closed-loop control to actuate the second valve during the second control as a function of measured values of the second sensor and based on a second control objective;

the second sensor being configured to measure an indicator of pressure and the second control objective being that the actual time course of pressure in the second duct follows a predefined desired pressure time course; or the second sensor being configured to measure an indicator of volume flow and the second control objective being that the actual time course of volume flow through the second duct follows a predefined desired volume flow time course.

4. The supply device in accordance with claim 1, further comprising a pneumatic control line pneumatically connected to the pressure reducer and pneumatically connected to the first duct at a branch point, wherein:

the pneumatic control line establishes a fluid connection between the first duct and the pressure reducer such that a time course of pressure in the pneumatic control line follows a time course of pressure at the branch point; and the pressure reducer is configured to cause the time course of the pressure at the back pressure outlet to follow the time course of the pressure in the pneumatic control line.

5. The supply device in accordance with claim 4, wherein a front pressure chamber connected or connectable to the second source via the front pressure inlet, a back pressure chamber connected to the second duct via the back pressure outlet, and a control pressure chamber are formed in an interior of the pressure reducer;

the pneumatic control line is in a fluid connection with the control pressure chamber such that a pressure in the control pressure chamber follows the pressure in the pneumatic control line; and the pressure reducer is configured such that the time course of a pressure at the back pressure outlet follows a time course of the pressure in the control pressure chamber.

6. The supply device in accordance with claim 5, wherein the pressure reducer comprises a partition wall with an opening and a closure for the opening;

the partition wall separates the front pressure chamber from the back pressure chamber;

the opening in the partition wall connects the front pressure chamber to the back pressure chamber;

the closure is configured to selectively release or to close the opening in the partition wall; and the pressure reducer is configured such that the closure releases the opening when a predefined criterion is met and otherwise closes the opening;

wherein the criterion depends on pressure in the control pressure chamber or on pressure in the back pressure chamber or on both pressure in the control pressure chamber and pressure in the back pressure chamber.

7. The supply device in accordance with claim 6, wherein:

the pressure reducer comprises a housing and a wall separates the back pressure chamber from the control pressure chamber;

the wall between the back pressure chamber and the control pressure chamber is movable relative to the pressure reducer housing or is flexible or is both movable and flexible such that a volume of the back pressure chamber and a volume of the control pressure chamber are variable; and the movable or flexible wall is in a functional connection with the closure for the opening in the partition wall.

8. The supply device in accordance with claim 1, further comprising:

a pressure sensor configured to measure an indicator of pressure at a measuring point in the first duct; and a signal-processing pressure-reducing control device configured to cause, depending on a signal of the pressure sensor, the time course of the pressure at the back pressure outlet to follow a time course of pressure at the reference point in the first duct.

9. The supply device in accordance with claim 8, wherein:

a back pressure chamber that is connected via the back pressure outlet to the second duct is formed in an interior of the pressure reducer;

the pressure reducer comprises an actuatable pressure reducer actuator;

the pressure-reducing control device is configured:

to actuate the pressure reducer actuator depending on a signal of the pressure sensor; and to cause, by the actuation, a time course of pressure in the back pressure chamber to follow the time course of the pressure at the reference point in the first duct.

10. The supply device in accordance with claim 9, wherein:

the pressure reducer comprises:

a front pressure chamber connectable to the second source via the front pressure inlet;

a partition wall with an opening; and a closure for the opening;

wherein the partition wall separates the front pressure chamber from the back pressure chamber;

wherein the opening in the partition wall connects the front pressure chamber to the back pressure chamber;

wherein the closure is configured to selectively release or close the opening in the partition wall; and the pressure reducer actuator is in a functional connection with the closure.

11. The supply device in accordance with claim 9, wherein a wall of the back pressure chamber is movable relative to another wall of the back pressure chamber such that a volume of the back pressure chamber is variable; and the pressure reducer actuator is in a functional connection with the movable wall.

12. The supply device in accordance with claim 1, in combination with a first source configured to provide the first gas component and with a second source configured to provide the second gas component to form a supply system for supplying the patient-side coupling unit with the gas mixture comprising the first gas component and the second gas component.

13. The supply device combination in accordance with claim 12, wherein the second source provides the second gas component with a higher pressure compared to a pressure with which the first source provides the first gas component.

14. The supply device in accordance with claim 1, further comprising:

a second sensor configured to measure an indicator of pressure in the second duct at a measuring location in the second duct or configured to measure an indicator of volume flow through the second duct at the measuring location in the second duct;

a second valve, the measuring location being located between the pressure reducer and the second valve.

15. The supply device in accordance with claim 14, further comprising:

a pneumatic resistance arranged between the pressure reducer and the measuring location.

16. A ventilation system for artificial ventilation of a patient with a gas mixture, the gas mixture comprising a first gas component and a second gas component, wherein at least one of the two gas components is oxygen or contains oxygen, the ventilation system comprising:

a fluid delivery unit;

a patient-side coupling unit connected or connectable to a patient; and a supply device comprising:

a first duct with a supply connection element configured to establish a fluid connection with a first source for the first gas component;

a second duct;

a mixing point;

an inhalation duct;

a pressure reducer with a front pressure inlet configured to establish a fluid connection with a second source for the second gas component and with a back pressure outlet, the back pressure outlet being connected to the second duct;

a first valve configured to change a volume flow through the first duct or a pressure in the first duct or both the volume flow through the first duct and the pressure in the first duct;

a first sensor configured to measure an indicator of pressure in the first duct or configured to measure an indicator of volume flow through the first duct; and a signal-processing control device configured to carry out a first closed-loop control to actuate the first valve during the first control as a function of measured values of the first sensor and based on a first control objective;

wherein the first duct is configured to guide the first gas component from the supply connection element to the mixing point, wherein the second duct is configured to guide the second gas component from the back pressure outlet to the mixing point, wherein the pressure reducer is configured to provide the second gas component such that a time course of pressure at the back pressure outlet follows a time course of pressure at a reference point in the first duct, wherein the inhalation duct is configured to guide a gas mixture generated or emerged at the mixing point to the patient-side coupling unit, wherein the ventilation system is configured to carry out ventilation strokes and to guide during each ventilation stroke a respective quantity of the gas mixture through the inhalation duct to the patient-side coupling unit, and wherein:

the first sensor is configured to measure an indicator of pressure, and the first control objective is the actual time course of pressure in the first duct to follow a predefined desired pressure time course; or the first sensor is configured to measure an indicator of volume flow, and the first control objective is the actual time course of volume flow through the first duct to follow a predefined desired volume flow time course.

17. The ventilation system in accordance with claim 16, wherein:

the signal-processing control device is further configured:

to derive a desired volume flow time course of the first gas component depending on a predefined desired time course of the volume flow of the gas mixture; and to actuate the first valve based on the first control objective.

18. The ventilation system in accordance with claim 16, further comprising:

a second valve configured to change a volume flow through the second duct; and a signal-processing control device configured:

to derive a desired volume flow time course of the second gas component depending on a predefined desired time course of the volume flow of the gas mixture; and to actuate the second valve based on a control objective, the control objective being the actual volume flow through the second duct being equal to the derived desired time course of the volume flow of the second gas component.

19. A supply process for supplying a patient-side coupling unit with a gas mixture, the gas mixture comprising a first gas component and a second gas component, wherein the patient-side coupling unit is connected or connectable to a patient, the supply process being carried out with a supply device comprising a first duct with a supply connection element, a second duct, a mixing point, an inhalation duct, a pressure reducer with a front pressure inlet and with a back pressure outlet, a first valve configured to change a volume flow through the first duct or a pressure in the first duct or both the volume flow through the first duct and the pressure in the first duct, a first sensor configured to measure an indicator of pressure in the first duct or configured to measure an indicator of volume flow through the first duct, and a signal-processing control device configured to carry out a first closed-loop control to actuate the first valve during the first control as a function of measured values of the first sensor and based on a first control objective wherein: the first sensor is configured to measure an indicator of pressure and the first control objective is the actual time course of pressure in the first duct to follow a predefined desired pressure time course; or the first sensor configured to measure an indicator of volume flow and the first control objective being the actual time course of volume flow through the first duct to follow a predefined desired volume flow time course;

the supply process comprises the steps of:

providing the first gas component at the supply connection element;

providing the second gas component at the front pressure inlet of the pressure reducer;

the pressure reducer providing the second gas component at its back pressure outlet;

causing a time course of a pressure at the back pressure outlet to follow a time course of pressure at a reference point in the first duct;

guiding the first gas component from the supply connection element to the mixing point with the first duct;

guiding the second gas component from the back pressure outlet of the pressure reducer to the mixing point with the second duct;

the gas mixture is generated or emerged at the mixing point; and guiding the gas mixture comprising the first gas component and the second gas component from the mixing point through the inhalation duct to the patient-side coupling unit.

20. The supply process in accordance with claim 19, wherein:

the supply device comprises a pneumatic control line;

the pneumatic control line is pneumatically connected to the pressure reducer and at a branch point to the first duct;

a time course of a pressure in the pneumatic control line follows a time course of a pressure at the branch point;

a time course of a pressure at the back pressure outlet follows the pneumatic control line pressure time course; and thereby the back pressure outlet pressure time course follows the time course of pressure at the reference point.

* * * * *